(12) United States Patent
Zhu et al.

(10) Patent No.: US 7,435,603 B2
(45) Date of Patent: *Oct. 14, 2008

(54) LABELING PROTEINS WITH DYES THAT ARE INSOLUBLE OR ONLY SPARINGLY SOLUBLE IN WATER

(75) Inventors: Mingde Zhu, Hercules, CA (US); Lee Olech, Rodeo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 11/249,683

(22) Filed: Oct. 12, 2005

(65) Prior Publication Data

US 2006/0052279 A1    Mar. 9, 2006

Related U.S. Application Data

(63) Continuation of application No. 10/278,745, filed on Oct. 21, 2002, now Pat. No. 6,995,023, which is a continuation-in-part of application No. 09/645,784, filed on Aug. 24, 2000, now abandoned.

(51) Int. Cl.
*G01N 33/533* (2006.01)
*C07D 309/00* (2006.01)
*C07H 23/00* (2006.01)

(52) U.S. Cl. ............... 436/546; 548/405; 536/26.6

(58) Field of Classification Search .............. None
See application file for complete search history.

(56) References Cited

U.S. PATENT DOCUMENTS

| | | | |
|---|---|---|---|
| 4,017,597 A | 4/1977 | Reynolds | |
| 4,142,044 A | 2/1979 | Günther et al. | |
| 4,180,060 A * | 12/1979 | Kutter | 600/573 |
| 4,309,316 A | 1/1982 | Lange et al. | |
| 4,649,193 A | 3/1987 | Meininger et al. | |
| 4,859,538 A | 8/1989 | Ribi | |
| 4,911,759 A | 3/1990 | Ohi et al. | |
| 5,274,113 A * | 12/1993 | Kang et al. | 548/405 |
| 5,352,246 A | 10/1994 | Hähnke et al. | |
| 5,366,870 A * | 11/1994 | Odstrchel et al. | 435/16 |
| 5,641,635 A | 6/1997 | Emmons et al. | |
| 5,695,990 A | 12/1997 | Cubicciotti | |
| 5,756,126 A | 5/1998 | Burgoyne | |
| 5,852,191 A * | 12/1998 | Karandikar et al. | 546/13 |
| 5,910,423 A * | 6/1999 | Yamazaki et al. | 435/28 |
| 5,997,907 A | 12/1999 | Goswami et al. | |
| 5,998,351 A | 12/1999 | Brouwer et al. | |
| 6,090,164 A | 7/2000 | Steckelberg et al. | |
| 6,664,047 B1 * | 12/2003 | Haugland et al. | 435/6 |
| 6,716,979 B2 | 4/2004 | Diwu et al. | |
| 6,995,023 B2 * | 2/2006 | Zhu et al. | 436/172 |

FOREIGN PATENT DOCUMENTS

| | | |
|---|---|---|
| CN | 11-38628 | 12/1996 |
| CN | 12-32867 | 10/1999 |

OTHER PUBLICATIONS

Collins Dictionary of Biology, definition for the term "solvent" (2005). Retrieved Apr. 6, 2007, from http://www.xreferplus.com/entry/5920573.*
Chan, K.C. et al. "Separation of tryptophan and related indoles by micellar electrokinetic chromatography with KrF laser-induced fluorescence detection," *J. of Chromatography A* 1995, pp. 203-210, vol. 718, No. 1.
Craig, D.B., et al., "Multiple Labeling of Proteins," *Anal. Chem.*, 1998, vol. 70, No. 13, pp. 2493-2494.
Csapo, Z. et al. "Automated ultra-thin-layer SDS gel electrophoresis of proteins using noncovalent fluorescent labeling," *Anal. Chem.* 2000, pp. 2519-1515, vol. 72.
Haughland, R.P. "Amine-reactive probes," *In Handbook of Fluorescent Probes and Research Chemicals*. 6th Edition. Molecular Probes, Inc., Eugene, OR 1999, pp. 1-5.
Haughland, R.P., *The Handbook: A Guide to Fluorescent Probes and Labeling Technologies* (web edition), Molecular Probes, 2005, www://probes.invitrogen.com), Section 1.4.
Material Safety Data Sheets, Molecular Probes, Inc., (Eugene, OR), Catalog No. A10192, Revised Aug. 3, 2004.

(Continued)

*Primary Examiner*—Long V. Le
*Assistant Examiner*—Christine E. Foster
(74) *Attorney, Agent, or Firm*—Townsend and Townsend and Crew LLP; Henry Heines

(57) ABSTRACT

The proteins in a biological sample that is sought to be analyzed for its protein composition by an electrophoretic or chromatographic procedure are coupled to a dye in an unusually efficient manner by combining the sample with a solid dry composition containing the dye, a buffering agent, and in preferred embodiments, a denaturing agent as well. The solid and dry form of the composition prevents the dye from deteriorating or decomposing, and the combination of components in the composition allows the dye to couple to the proteins in a relatively uniform manner with no overstaining of the protein when the composition and the sample are heated together and held at an elevated temperature for a short period of time.

8 Claims, No Drawings

OTHER PUBLICATIONS

Mujumdar, R.B. et al. "Cyaninedye labeling reagents: Sulfoindocyanine succinimidyl esters," *Bioconjugate Chem*, Mar./Apr. 1993, pp. 105-111, vol. 4, No. 2.

Pinto, D.M. et al. "Picomolar assay of native proteins by capillary electrophoresis precolumn labeling, submicellar separation, and laser-induced fluorescence detection," *Anal. Chem.* 1997, pp. 3015-3021, vol. 69, No. 15.

Shea, D. "Analysis of brevetoxins by micellar electrokinetic capillary chromatography and laser-induced fluorescence detection," *Electrophoresis*, Feb. 1997, pp. 277-283, vol. 18, No. 2.

Sigma Chemical Compound Catalog Of Biochemicals "Organic compounds for research ands diagnostic reagents," 1992, pp. 933, 1641, 1646.

Sigma Catalog of Biochemicals and Reagents for Life Science Research, 2000-2001, St. Louis, MO, p. 801.

Strottmann, J.M., et al., "Advantages of preelectrophoretic conjugation of polypeptides with fluorescent dyes," *Anal. Biochem.*, 1983, vol. 132, No. 2, pp. 334-337.

Unlu, M., et al., "Difference gel electrophoresis: A single gel method for detecting changes in protein extracts," *Electrophoresis*, 1997, vol. 18, pp. 2071-2077.

Urwin, V.E. and Jackson, P. "Two-dimensional polyacrylamide gel electrophoresis of proteins labeled with the fluorophore monobromobimane prior to first-dimensional isoelectric focusing: Imaging of the fluorescent protein spot patterns using a cooled charge-coupled device," *Anal. Biochem.* 1993, pp. 57-62, vol. 209.

Epand, Raquel F. et al.; "The antimicrobial peptide trichogin and its interaction with phospholipid membranes"; 1999, *Eur. J. Biochem.*, vol. 266, pp. 1021-1028.

Lakowicz, Joseph R. et al.; "Increased Intensities of YOYO-1-labeled DNA Oligomers Near Silver Particles"; 2003, *Photochemistry and Photobiology*, vol. 77, No. 6, pp. 604-607.

So, Peter T.C. et al.; "Two-Photon Excitation Fluorescence Microscopy"; 2000, *Annu. Rev. Biomed. Eng.*, vol. 2, pp. 399-429.

Varadarajan, Navin et al.; "Engineering of protease variants exhibiting high catalytic activity and exquisite substrate selectivity"; 2005, *Proc. Natl. Acad. Sci.*, vol. 102, No. 19, pp. 6855-6860.

Zegers, Mirjam M.P. et al.; "Mechanisms and functional features of polarized membrane traffic in epithelial and hepatic cells"; 1998, *Biochem. J.*, vol. 336, pp. 257-269.

\* cited by examiner

LABELING PROTEINS WITH DYES THAT ARE INSOLUBLE OR ONLY SPARINGLY SOLUBLE IN WATER

CROSS-REFERENCE TO RELATED APPLICATION

This application is a continuation of application Ser. No. 10/278,745, filed Oct. 21, 2002, which is a continuation-in-part of application Ser. No. 09/645,784, filed Aug. 24, 2000, now abandoned, and all of the foregoing applications are incorporated herein in their entirety for all purposes capable of being served thereby.

BACKGROUND OF THE INVENTION

The analysis of biological samples to determine the identity and amounts of various proteins for diagnostic or research purposes is performed by a wide variety of separation techniques, many of which involve the use of dyes to enable the clinician to locate, identify, and quantitate the proteins. The dyes are detectable and readable by visual observation or are machine-readable. Included among the many types of dyes that are used for this purposes are those that emit colors in the visible range or the ultraviolet range to the eye without treatment or activation, and fluorescent dyes which emit upon excitation.

The dyes are most commonly applied to the proteins after separation has occurred and while the proteins are isolated into individual spots or bands in the gel. Applying the dyes in this manner and removing excess dye is a labor-intensive and time-consuming procedure that is susceptible to handling difficulties, operator error and various nonuniformities. Dyes that are insoluble or poorly soluble in water must first be dissolved in an organic solvent before being applied to the protein spots or bands in the gel. As an alternative, dyes can be applied to the proteins in the sample before the separation is performed. This also involves first dissolving the dyes in an organic solvent. One difficulty with these methods is that the ratio of dye to protein must be carefully controlled to avoid overstaining the proteins. Overstaining can cause nonuniformities among the various different proteins in the amount of dye that is coupled to each protein. Overstaining can also change the apparent mobilities of the proteins during electrophoresis, and this can occur to different degrees among different proteins, particularly when the proportion of dye to protein is nonuniform.

One of the areas in which these dyes are used is the electrophoresis of proteins under denaturing conditions. Denaturing electrophoresis, and particularly SDS-PAGE (sodium dodecyl sulfate polyacrylamide gel electrophoresis), is a highly effective and efficient means of analyzing proteins in a sample, since it identifies proteins independently of the potentially interfering influences of tertiary or quaternary shape or the complexity of their subunits. The concerns raised by the use of dyes apply with particular force to denaturing electrophoresis in view of its widespread use and effectiveness.

SUMMARY OF THE INVENTION

It has now been discovered that fluorescent dyes that are insoluble or at most sparingly soluble in water can be applied to biological samples in an unusually efficient manner by using the dye in solid dry form in the presence of a non-nucleophilic buffering agent and in the absence of organic solvents. In certain embodiments of the invention, a denaturing agent is also present. The solid dry composition can be either a powder that is added to the biological sample or a dry coating on the inner surface of a sample tube or other receptacle, such as a test tube or cuvette, in which the sample is placed. When the composition is a powder, it preferably contains the buffering agent and the denaturing agent and is suspended in the liquid sample. When the composition is a coating on the inner surface of a receptacle, the coating preferably contains the dye plus a polymer that controls the rate of dissolution of the dye into the sample, and the buffering agent and denaturing agent are added as a separate aqueous solution. In either case, the coupling of the dye to the proteins in the sample is achieved by contacting the sample with the solid dry composition in the absence of organic solvents and, while the sample and composition are in contact, heating the sample to an elevated but non-boiling temperature for a period of time sufficient to achieve coupling between the dye and the protein. The result is a substantially consistent relative staining of the proteins in the sample, i.e., an approximately even amount of dye among the various proteins in the sample, with substantially no change in the apparent mobilities of the proteins, i.e., the amount of dye on each protein is small enough to have only a minimal effect on the separation behavior of each protein relative to the other proteins in the sample. This uniform staining is achieved over a wide range of dye-to-protein ratios.

The solution thus prepared is ready for loading onto a separation medium where it can be separated by conventional protein separation procedures known in the art. These procedures include the various forms of electrophoresis as well as other protocols. The individual protein bands or spots that result from the separation are discernable either by machine reading or by visual observation.

This invention also resides in a receptacle coated with the solid dry composition described above.

DETAILED DESCRIPTION OF THE INVENTION

Dyes that can be used in the solid dry composition of this invention include fluorescent dyes whose solubility in water is less than $5 \times 10^{-6}$ g/cc (i.e., less than 5 µg/mL), preferably less than $0.3 \times 10^{-6}$ g/cc (i.e., less than 0.3 µg/mL). Preferred dyes are those that can be excited by light at a wavelength between 400 nm and 700 nm, since glass and plastic, the materials used in the construction of electrophoresis gel cassettes, absorb and fluoresce less within this wavelength range.

Included among these dyes are electrophilic-activated forms of fluorescent dyes including, but not limited to, succinimidyl esters, vinyl sulfones, etc., of xanthenes, cyanines, coumarins, benzimides, phenanthridines, ethidium dyes, acridine dyes, carbazole dyes, phenoxazine dyes, porphyrin dyes, and quinoline dyes. Succinimidyl groups are of particular interest as the reactive group on the dye, since the succinimidyl group reacts efficiently with a primary amino group on a peptide, and succinimidyl esters are more stable in aqueous solutions than other amino reactive agents such as isothioicyanates. Fluoresceins and rhodamines are particular types of xanthene dyes. Specific examples are 6-carboxyfluorescein, 6-carboxy-4',5'-dichloro-2',7'-dimethoxyfluorescein, N,N,N',N'-tetramethyl-6-carboxyrhodamine, 6-carboxy-X-rhodamine, 5-carboxyrhodamine-6G, 5-carboxyrhodamine-6G, tetramethylrhodamine, Rhodamine Green, and Rhodamine Red. Umbelliferone is an example of a coumarin. Hoechst 33258 is an example of a benzimide dye. Texas Red is an example of a phenanthridine dye. Examples of cyanine succinimidyl ester dyes are sulfoindocyanine succinimidyl esters, (carboxyalkyl)cyanines succinimidyl esters, and BODIPY succinimidyl esters (Molecular Probes, Inc.). Preferred dyes are fluorophores that do not contain a charged group, either positive or negative, and that exhibit both low solubility and low bias to certain proteins relative to others. Examples of dyes that meet this description are are 4,4-difluoro-5,7-diphenyl-4-bora-3a,4a-diaza-s-indacene-3-propionic acid, succinimidyl ester (BODIPY® 530/550, SE), 4,4-difluoro-5,7-dimethyl-4-bora-3a,4a-diaza-s-indacene-3-propionic acid, succinimidyl ester (BODIPY® 502/510, SE), and 6-(((4,4-difluoro-5-(2-pyrrolyl)-4-bora-3a,4a-diaza-s-indacene-3-yl)styryloxy)acetyl)aminohexanoic acid, succinimidyl ester (BODIPY® 650/665-X, SE).

The non-nucleophilic buffering agent serves to limit the rate of hydrolysis of the dye and thereby the rate at which the dye becomes available for coupling to the protein when the dye is placed in contact with the biological sample. Suitable buffering agents are those that do not compete with the protein for coupling to the dye. Preferred buffering agents are those that have a pH range of about 8.0 to about 9.5, and those that do not contain thiols or primary or secondary amines. Examples of buffering agents that meet this description are sodium borate, sodium carbonate, and N-2-hydroxyethylpiperazine-N'-2-ethanesulfonic acid (HEPES). A further preferred buffering agent, one that contains an amino group that does not compete with the amino group on the protein for coupling to the dye, is tris(hydroxymethyl)aminomethane.

In the preferred practice of the invention, the contact between the sample and the dye is done in the presence of a protein denaturing agent. This permits protein denaturation and labeling to be performed in a single step. Conventional denaturing agents may be used, examples of which are sodium dodecyl sulfate (SDS), urea, and guanidine. The most preferred is SDS. Other substances may also be included on an optional basis. Examples are sugars (such as sucrose) for density adjustment and a tracking indicator to indicate the location of the moving solute front during the separation process. The tracking indicator can be any indicator that is inert toward the proteins and other components included in either the solid dry composition or the biological sample. One example of such an indicator is Bromophenol Blue. A reducing agent (in solid form) can also be included. Examples of suitable reducing agents are dithiothreitol, dithioerythritol, and tris(carboxyethyl)phosphine. Still further examples of each of these additives will be readily apparent to those skilled in the art.

The relative amounts of each component in the solid dry composition are not critical to the invention and may vary. In a typical composition that contains both the active dye (i.e., the dye that couples to the proteins) and an indicator dye (the dye that is included to show the location of the moving ion front), plus SDS as a denaturing agent, sucrose as a density adjusting agent, and sodium borate as the buffer, preferred amounts of each for a final volume of 1.0 mL are as follows:

| | |
|---|---|
| Active dye | 2-100 µg |
| Denaturing agent, such as SDS | 0-20 mg |
| Density adjusting agent, such as sucrose | 0-400 mg |
| Buffer, such as sodium borate | 2-20 mg |
| Indicator dye | 0-200 µg |

In embodiments of the invention in which the solid dry composition is a powder mixture, the particle size of the powder mixture is not critical to the invention and can vary. A preferred particle size range is from about 5 microns to about 500 microns. The preparation and size control of the particles in the mixture is achieved by conventional methods, including precipitation, grinding, sieving, and other methods that will be readily apparent to those skilled in the art.

In these embodiments, the powder mixture is combined with the biological sample either immediately prior to or a short period of time before the sample is applied to the separation medium for analysis. The powder mixture can first be mixed with water to form a preliminary solution that is subsequently combined with the biological sample. In other embodiments of the invention, the powder mixture is combined directly with the sample, and the powder and sample are heated to a temperature high enough, and for a period of time long enough, to cause coupling between the dye and the proteins in the sample yet not so high as to cause the sample to boil. Preferred temperatures are in the range of from about 80° C. upward, more preferably about 90° C. to about 100° C., and most preferably about 95° C. In most cases, acceptable results will be achieved in a few minutes, preferably about five minutes. The solution is then cooled and loaded into the separation system.

In embodiments of the invention in which the solid dry composition is a coating on the wall of a receptacle, the receptacle can be any vessel in which a liquid biological sample can be retained. Examples are test tubes, cuvettes, and wells in multi-well plates. The coating can be applied by conventional techniques, including the application of the coating as a suspension or a solution in an organic solvent, followed by the evaporation of the suspending medium or the solvent. The coating mixture can also contain a polymer such as polyvinyl alcohol, polyethylene glycol, or polyvinylpyrrolidone to serve as a binder to promote the adherence of the coating on the receptacle wall prior to contact with the sample. The amount of polymer may vary and is not critical, although preferred weight ratios of polymer to dye are from about 1:1 to about 10:1.

As one example of an implementation of this invention in which the dye is a coating on the wall of a microplate tube, the dye is dissolved in isopropanol to a concentration of 50 µg/mL, and 50 µL of the resulting solution are placed in the tube. The isopropanol is then evaporated from the tube by a vacuum pump leaving a coated tube that is then stored in a dark, cold, dry environment until ready for use. When a sample is ready for coupling of its proteins to the dye in the coating, the sample is combined with an aqueous buffer solution in the microplate tube and the tube and its contents are incubated at 95° C. for 5 minutes. The buffer solution contains 50 mM NaHCO$_3$, pH 8.5, 1% SDS, and 25% sucrose.

This invention is useful in preparing biological samples for a wide variety of separation procedures that involve the use of dyes for differentiation and identification of the different proteins. Included among these procedures are ion exchange chromatography, hydrophobic interaction chromatography, affinity chromatography, molecular sieve chromatography, adsorption chromatography, exclusion chromatography, and various forms of electrophoresis, including isoelectric focusing and conventional electrophoresis in either a capillary, tube gel, or slab gel configuration, or microchannels on a microfluidics chip. The invention is particularly useful in two-dimensional electrophoresis, where the first dimension is a linear separation in a rod-shaped or strip-shaped gel and the second is performed by placing the rod or strip along one edge of a slab gel for migration of the bands laterally out of the rod or strip and into the slab in a direction perpendicular to the axis of the rod or strip. Separation media for the various forms of electrophoresis include polyacrylamide, cellulose, agarose, dextran, polyvinylalcohol, starch, silica gel, and polymers of styrene and divinylbenzene, as well as combinations of these materials. Polyacrylamide gel electrophoresis is of particular interest.

The foregoing is offered primarily for purposes of illustration. Further modifications and variations of the various parameters of the composition and method of this invention will be readily apparent to those skilled in the art and are included within the scope of the invention.

What is claimed is:

1. A process for the preparation of a protein-containing biological sample for electrophoretic analysis of protein composition of said sample, said process comprising:
   (a) placing said sample in a receptacle having an inner surface with a solid dry coating thereon, said coating comprising a cyanine succinimidyl ester fluorescent dye whose solubility in water is less than 5 µg/mL at 25° C. and which is capable of coupling to a protein, in the absence of organic solvents; and
   (b) while said sample is in said receptacle and in contact with said coating and a non-nucleophilic buffering agent, heating said sample to a non-boiling temperature of at least about 80° C. to cause said fluorescent dye to couple to said protein.

2. A process in accordance with claim 1 in which said solid dry coating further comprises a protein denaturing agent.

3. A process in accordance with claim 2 in which said protein denaturing agent is sodium dodecyl sulfate.

4. A process in accordance with claim 1 in which said non-nucleophilic buffering agent is a buffering agent that maintains a pH within the range of about 8.0 to about 9.5 when dissolved in aqueous solution.

5. A process in accordance with claim 1 in which said non-nucleophilic buffering agent is a member selected from the group consisting of sodium borate, sodium carbonate, and N-2-hydroxyethylpiperazine-N'-2-ethanesulfonic acid.

6. A process in accordance with claim 1 in which said receptacle is a sample tube, and step (a) comprises placing said sample in said sample tube.

7. A process in accordance with claim 6 in which step (a) comprises placing said sample and an aqueous solution in which are dissolved said non-nucleophilic buffering agent and a protein denaturing agent in said sample tube.

8. A process for the preparation of a protein-containing biological sample for electrophoretic analysis of protein composition of said sample, said process comprising:
   (a) placing said sample in a receptacle having an inner surface with a solid dry coating thereon, said coating comprising a succinimidyl ester of a 4,4-difluoro-4-bora-3a,4a-diaza-s-indacene-based dye whose solubility in water is less than 5 µg/mL at 25° C. and which is capable of coupling to a protein, in the absence of organic solvents; and
   (b) while said sample is in said receptacle and in contact with said solid dry coating and a non-nucleophilic buffering agent, heating said sample to a non-boiling temperature of at least about 80° C. to cause said succinimidyl ester to couple to said protein.

* * * * *